United States Patent
Ghalili

(10) Patent No.: US 11,376,227 B2
(45) Date of Patent: Jul. 5, 2022

(54) CANNABINOID AND MENTHOL GUM AND LOZENGE COMPOSITIONS AND METHODS

(71) Applicant: Babak Ghalili, New York, NY (US)

(72) Inventor: Babak Ghalili, New York, NY (US)

(*) Notice: Subject to any disclaimer, the term of this patent is extended or adjusted under 35 U.S.C. 154(b) by 0 days.

(21) Appl. No.: 16/807,281

(22) Filed: Mar. 3, 2020

(65) Prior Publication Data
US 2020/0315988 A1    Oct. 8, 2020

Related U.S. Application Data

(63) Continuation-in-part of application No. 16/555,022, filed on Aug. 29, 2019.

(60) Provisional application No. 62/869,121, filed on Jul. 1, 2019, provisional application No. 62/726,713, filed on Sep. 4, 2018.

(51) Int. Cl.
| A61K 31/045 | (2006.01) |
| A61K 36/185 | (2006.01) |
| A61K 31/194 | (2006.01) |
| A61K 9/68 | (2006.01) |
| A61K 9/00 | (2006.01) |

(52) U.S. Cl.
CPC .......... *A61K 31/045* (2013.01); *A61K 9/0056* (2013.01); *A61K 9/0058* (2013.01); *A61K 31/194* (2013.01); *A61K 36/185* (2013.01)

(58) Field of Classification Search
CPC ............................ A61K 6/0056; A61K 6/0058
See application file for complete search history.

(56) References Cited

U.S. PATENT DOCUMENTS

| 4,088,788 | A | * | 5/1978 | Ream | A23G 4/06 |
| | | | | | 426/3 |
| 5,869,087 | A | | 2/1999 | Hirano et al. | |
| 6,495,097 | B1 | * | 12/2002 | Streit | A61K 8/361 |
| | | | | | 422/120 |
| 9,433,601 | B2 | | 9/2016 | Damme et al. | |
| 10,420,809 | B2 | | 9/2019 | Crowley | |
| 2004/0028772 | A1 | * | 2/2004 | Andersen | A61K 9/0058 |
| | | | | | 426/3 |
| 2005/0002993 | A1 | | 1/2005 | Goggin et al. | |
| 2006/0280834 | A1 | | 12/2006 | Jani et al. | |
| 2009/0036523 | A1 | | 2/2009 | Stinchcomb et al. | |
| 2010/0074988 | A1 | | 3/2010 | Jeon et al. | |
| 2011/0097283 | A1 | | 4/2011 | Damme et al. | |
| 2011/0207817 | A1 | | 8/2011 | Wetterer et al. | |
| 2013/0005831 | A1 | | 1/2013 | Rajewski et al. | |
| 2014/0271940 | A1 | * | 9/2014 | Wurzer | A61P 25/00 |
| | | | | | 424/725 |
| 2015/0017105 | A1 | * | 1/2015 | Borja | A23L 29/20 |
| | | | | | 424/49 |
| 2015/0374770 | A1 | | 12/2015 | Crowley | |
| 2017/0239359 | A1 | | 8/2017 | Boija et al. | |
| 2018/0110730 | A1 | | 4/2018 | Changoer et al. | |

FOREIGN PATENT DOCUMENTS

| WO | WO-2006127481 A2 * | 11/2006 | ............... A23G 4/20 |
| WO | 2014159688 A1 | 10/2014 | |

OTHER PUBLICATIONS

"What does Full-Spectrum Hemp Oil Mean?", downloaded Aug. 30, 2020 from the Web Archive at https://web.archive.org/web/20160803153001/https:// medicalmarijuanainc.com/full-spectrum-hemp-oil; available on the Web Aug. 3, 2016 (Year: 2016).*
Scifinder Search_8-31-2020_menthol stabilization with fatty acids (Year: 2020).*
T.Krizek, et al. Menthol-based hydrophobic deep eutectic solvents: Towards greener and efficient extraction of phytocannabinoids, Journal of Cleaner Production 193 (2018) 391-396. (Year: 2018).*
Google search, Jan. 20, 2021 (Year: 2021).*
Google_scholar_search_8-11-21_Can_ester_do_hydrogen_bonding_with_an_alcohol (Year: 2021).*
Google_scholar_search_8-11-21_hydrogen_bonding_with_carboxylate_salt_and_carboxylic_acid (Year: 2021).*
Google_Scholar_deep_eutectic_system_menthol_-_8-11-21 (Year: 2021).*
Faisal Al-Akayleh, et al. Therapeutic deep eutectic system of capric acid and menthol: Characterization and pharmaceutical application. Journal of Drug Delivery Science and Technology 53 (2019) 101159 1-10. (Year: 2019).*
T. Fan et al. Preparation of menthol-based hydrophobic deep eutectic solvents for the extraction of and extraction mechanism. Analyst, 2021, 146, 1996-2008. [utilized for definitions only] (Year: 2021).*
E. Muzenda. Interactions of Polar and Nonpolar Volatile Organic Compounds with Methyl Ester Solvents. 3rd International Conference on Medical Sciences and Chemical Engineering (ICMSCE'2013) Dec. 25-26, 2013 Bangkok (Thailand), 22-26. (Year: 2013).*
Abualhasan et al. "GC Method Validation for the Analysis of Menthol in Suppository Pharmaceutical dosage Form" International Journal of Analytical Chemistry, vol. 2017, Article ID 1728414, Mar. 6, 2017, 9 Pages.
Canchew. Nutraceuticals, 2019, Retrieved from Internet URL: 1 Page.
Galeotti et al. "Menthol: a natural analgesic compound" Neuroscience Letters 322 (2002) pp. 145-148, 4 Pages.

(Continued)

*Primary Examiner* — Michael P Cohen
(74) *Attorney, Agent, or Firm* — Ziegler IP Law Group, LLC

(57) ABSTRACT

The present disclosure relates to chewing gum or lozenge with cannabinoids and menthol including a liquid-filled chewing gum or lozenge with a chewing gum base shell or lozenge candy shell enclosing an internal void therein and a liquid filling in the void, the liquid-filled chewing gum or lozenge including cannabinoids and menthol. The menthol component can be a stabilized menthol composition comprising menthol and at least one menthol stabilizer compound including undecylenic acid methyl ester, undecylenic acid or a salt of undecylenic acid.

22 Claims, 4 Drawing Sheets

(56) References Cited

OTHER PUBLICATIONS

Hyrup et al. "The MediChew technology platform" Expert Opinion. Drug Deliv (2005) 2(5) p. 927-933, 7 Pages.

Notification of Transmittal of the International Search Report and the Written Opinion of the International Searching Authority, or the Declaration, Application No. PCT/US19/48740, dated Jan. 17, 2020.

Notification of transmittal of the International Search Report and the written opinion of the International Searching Authority, or the Declaration, Application No. PCT/US20/20733, dated Jun. 16, 2020, 21 Pages.

Selhub. Will this Hemp-based Oil Replace Opioids & OTC Pain Relievers. May 26, 2018, Retrieved Nov. 1, 2011, Retrieved from Internet URL, 1 Page.

\* cited by examiner

CANNABINOID AND MENTHOL GUM AND LOZENGE COMPOSITIONS AND METHODS

CROSS-REFERENCE TO RELATED APPLICATIONS

This application is a continuation-in-part of U.S. patent application Ser. No. 16/555,022 filed Aug. 29, 2019 which claims priority to and the benefit of U.S. Provisional Patent Application Ser. No. 62/726,713 filed Sep. 4, 2018 and U.S. Provisional Patent Application Ser. No. 62/869,121 filed Jul. 1, 2019, the disclosures of which is incorporated herein by reference in its entirety.

FIELD

The aspects of the present disclosure relate to compositions including active agents such as cannabinoids and menthol.

BACKGROUND

There is a need for novel treatments for pain and inflammation. Some current agents may be ineffective and can, for example, come with unacceptable side effects. Furthermore, there is a growing concern about the overuse of opioid pain treatments.

It is well known to use chewing gum and lozenges can be used as an oral delivery means for various therapeutic compounds to a user with appropriate doses of the therapeutic compound.

A problem is, however, how to incorporate such therapeutic compounds such as cannabinoids and menthol into a chewing gum or lozenge so as to effectively deliver it to the user while maintaining its activity.

It is an object of the present disclosure to obtain a chewing gum/lozenge that includes cannabinoids and menthol.

SUMMARY

These and other aspects and advantages of the exemplary embodiments will become apparent from the detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

In one embodiment, a chewing gum or lozenge product is provided. The chewing gum or lozenge product includes at least one cannabinoid is in an amount of from about 0.1 wt % to about 10 wt %. and an effective amount of menthol comprising a stabilized menthol composition including menthol and at least one menthol stabilizer compound including undecylenic acid methyl ester, undecylenic acid or a salt of undecylenic acid.

In another embodiment, a filled chewing gum or lozenge product is provided. The filled chewing gum or lozenge product includes a shell enclosing an internal void therein and a filling in the void, the filled chewing gum or lozenge product including at least one of full spectrum hemp oil in an amount of from about 0.1 wt % to about 10 wt % and menthol in an amount of from about 0.1 wt % to about 14 wt %, wherein the menthol is included in a stabilized menthol composition comprising menthol and at least one menthol stabilizer compound including undecylenic acid methyl ester, undecylenic acid or a salt of undecylenic acid.

In another embodiment a method of treating pain of a patient using a chewing gum or lozenge product. The chewing gum or lozenge product is a unit dose formulation and includes full spectrum hemp oil in a unit dose amount of from about 2 mg. to about 30 mg. and menthol in a unit dose amount of from about 1 mg. to about 20 mg, wherein the menthol is included in a stabilized menthol composition comprising menthol and at least one menthol stabilizer compound including undecylenic acid methyl ester, undecylenic acid or a salt of undecylenic acid. The method includes orally administering the chewing gum or lozenge product to an oral cavity of the patient.

DESCRIPTION OF THE DRAWINGS

The accompanying drawings illustrate presently preferred embodiments of the present disclosure, and together with the general description given above and the detailed description given below, serve to explain the principles of the present disclosure.

DETAILED DESCRIPTION

Figure 1A:
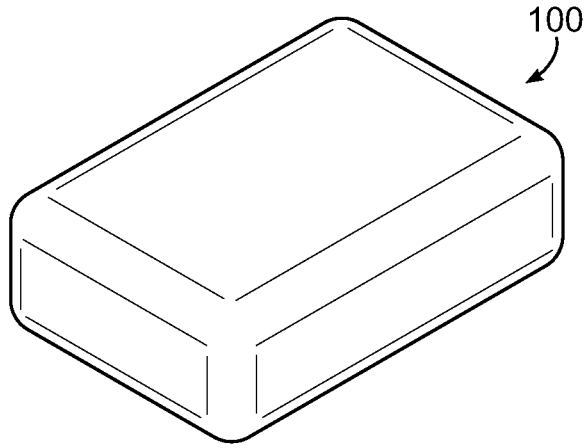
FIG. 1A is illustrative of an exterior perspective view of an exemplary center-filled chewing gum embodiment of the present disclosure.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The terms "oral acceptable" or "dentally acceptable" means the compound, substance or device may be administered to or into the oral cavity and/or surfaces of the oral cavity, including the teeth and gums, without substantial harmful effects to the oral cavity and/or its surfaces.

The term "pharmaceutically acceptable" means that which is useful in preparing a pharmaceutical composition that is generally non-toxic and is not biologically undesirable and includes that which is acceptable for veterinary use and/or human pharmaceutical use.

Chewing gum and lozenges, including those that are liquid-filled, and methods of making and using them are disclosed in the following: U.S. Pat. Nos. 9,253,991; 3,806,290; 3,857,963; 4,250,196; 4,252,829; 4,642,235; 5,916,606; 9,839,693; and 5,922,347, the disclosures of which is hereby incorporated by reference in its entirety.

The aspects of the disclosed embodiments relate to chewing gum and lozenge compositions (e.g., chewing gum and lozenges that are liquid-filled) for the delivery of an active agent(s). The aspects of the disclosed embodiments also relate to processes for the preparation of, intermediates used in the preparation of, compositions (e.g., pharmaceutical, medical device cosmetic, industrial) containing and the uses of such chewing gum and lozenges in the treatment of disorders or application of specified agents to a surface.

The aspects of the present disclosure relate to chewing gum (also referred to herein as "gum") and lozenge compositions, products and devices (e.g., chewing gum and lozenges including those that are unfilled and filled including liquid-filled or solid or semi-solid filled) used to relieve local and/or systemic pain (i.e., analgesics) and/or inflammation, methods of making such compositions, products and devices and methods of using such compositions, products and devices including, for example, orally administered (e.g., placed in the mouth) compositions including pharmaceutical compositions, products and devices including analgesic and/or anti-inflammatory pharmaceutical compositions, products and devices for the treatment of pain and/or inflammation, that contain a pharmaceutically effective amount of a pharmaceutically acceptable and effective cannabinoid, a pharmaceutically effective amount of menthol and a pharmaceutically acceptable carrier for example, chewing gum and lozenges including those that are unfilled and filled including the fill (e.g., liquid filled or solid or semi-solid filled) and/or shell of the chewing gum or lozenge. Such chewing gum and lozenge compositions, products and devices (e.g., chewing gum and lozenges including those that are unfilled and filled including liquid-filled or solid or semi-solid filled) may also include, for example, oral care compositions, products and devices for the treatment of oral or dental pain, including oral care analgesic and/or anti-inflammatory compositions, for the treatment of oral or dental pain and/or inflammation that contain a pharmaceutically effective amount of an oral or dental acceptable and effective cannabinoid, a pharmaceutically effective amount of menthol and an oral or dental acceptable carrier in, for example, the liquid fill of the chewing gum or lozenge. Such chewing gum and lozenge compositions, products and devices (e.g., chewing gum and lozenges including those that are unfilled and filled including liquid-filled or solid or semi-solid filled) may also include, for example, analgesic and/or anti-inflammatory pharmaceutical compositions, products and devices for the treatment of local and/or systemic pain and/or inflammation that contain a pharmaceutically effective amount of a pharmaceutically acceptable and effective cannabinoid, a pharmaceutically effective amount of menthol and a pharmaceutically acceptable carrier in, for example, the liquid fill and/or shell of the chewing gum or lozenge. Such chewing gum and lozenge compositions, products and devices (e.g., chewing gum and lozenges including those that are unfilled and filled including liquid-filled or solid or semi-solid filled) may also include, for example, oral care analgesic and/or anti-inflammatory compositions, products and devices for the treatment of oral or dental pain and/or inflammation, including oral care analgesic and/or anti-inflammatory compositions, products and devices, that contain a pharmaceutically effective amount of an oral or dental acceptable and effective cannabinoid, a pharmaceutically effective amount of menthol and an oral or dental acceptable carrier in for example, the liquid fill and/or shell of the chewing gum or lozenge.

The combination of cannabinoid and menthol into a single therapeutic composition, for example, chewing gum and lozenge compositions (e.g., chewing gum and lozenges that are liquid-filled), can provide improved and better focused delivery of the actives to a patient than separately applying the cannabinoid and menthol separately (to different areas of the body or layered one on top of another).

Orally administered including oral care and other pharmaceutical compositions, products and devices of the present disclosure include products which, in the ordinary course of usage, can be chewed or sucked on in the mouth to release the active ingredients (e.g., cannabinoid, menthol, etc.) therein, for example, from the composition itself or shell dissolving and/or the release and/or dissolving of the fill of the chewing gum or lozenge (e.g., to deliver the therapeutic in and through the mouth tissues or in the body past the oral cavity, e.g., the GI tract), or are not intentionally swallowed initially and remains there for a period of time process for purposes of local and/or systemic administration of particular therapeutic agents, but is rather retained in the oral cavity or the tissues thereof during the chewing/sucking for a time sufficient to be effective for purposes of therapeutic activity within the oral cavity, surfaces and tissues therein as well as systemic delivery and through the swallowing of dissolved (e.g., from the shell) or released (e.g., from the center filling material) that passes pas the mouth and into the GI tract where it is absorbed. After being present in the oral cavity for a time sufficient to be effective for purposes of therapeutic activity, they can be removed from the oral cavity or swallowed or chewed and pass through the digestive system for removal. Teeth, as used herein, refers to natural teeth as well as artificial teeth or dental prosthesis. Oral cavity includes teeth, tissues (including mucous membranes and cheek tissue in the oral cavity) and the surfaces thereof present in mouth. The composition, products and devices of the present disclosure may, for example, be administered to patients with oral pain, such as tooth pain, and pain from gums or cheeks following dental procedures, as wells as patients with bleeding gums or areas in the mouth that are suspect to infection as well as systemic pain in other parts of the body.

"Pain" as referred to herein for the composition and method embodiments of the current disclosure and for which an analgesic or pain relieving or pain treating composition or component thereof treats includes, but is not limited to local pain, systemic pain, oral pain, dental pain and general pain, regardless of the location on the body to which the embodiment of the current disclosure is administered.

"Anti-inflammatory" as referred to herein for the composition and method embodiments of the current disclosure and for which an anti-inflammatory composition or component thereof treats includes, but is not limited to local inflammation, systemic inflammation, oral inflammation, dental inflammation and general inflammation, regardless of the location on the body to which the embodiment of the current disclosure is administered.

Cannabinoids are an active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure. Cannabinoids can also have therapeutic value as a nutrient and can be included in composition and method embodiments of the present disclosure in an effective amount to perform that function.

Examples of phytocannabinoids include Cannabidiol (CBD) including, for example, CBD oil, Cannabinol (CBN) and tetrahydrocannabinol (THC), the latter being a known psychotropic compound and the first two being non-psychotropic. *Cannabis* plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and cannabinoids included herein (unless otherwise stated) have minimal levels of THC (less than 0.3%). Examples of oral or pharmaceutically effective cannabinoids include CBD (for example, CBD oil). Cannabinoid, including, for example, phytocannabinoids including CBD, can be in an amount of about 0.1 wt % to about 20 wt %, about 0.1 wt % to about 10 wt %, 0.1 wt % to about 1 wt %, about 0.5 wt % to about 6 wt % or about 5.7 wt %. CBD can be in an amount of about 0.1 wt % to about 20 wt %, about 0.5 wt % to about 5 wt %, about 0.5 wt % to about 2 wt % or about 1.9 wt %. Unit dosage formulations of the embodiments of the present disclosure can include cannabinoid, for example, a phytocannabinoid (including for example, CBD) in the amount of about 2 mg. to about 60 mg., about 5 mg. to about 30 mg., about 5 mg. to about 15 mg., about 15 mg. to about 30 mg. or about 30 mg. to about 45 mg. Unit dosage formulations of the embodiments of the present disclosure can include CBD in the amount of about 2 mg. to about 30 mg., about 5 mg. to about 30 mg., about 5 mg. to about 15 mg., about 15 mg. to about 30 mg. or about 10 mg. Unit doses of CBD oil content can include an amount of about 2 mg. to about 60 mg. An effective amount of cannabinoid includes an analgesic, pain relieving, pain treating or anti-inflammatory amount of cannabinoid.

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil, CBD oil, full spectrum hemp oil and full spectrum CBD oil, *Cannabis sativa* seed oil, etc.) that include one or a plurality of phytocannabinoids.

Full spectrum hemp oil is oil derived from the entire plant except the flower (which contains THC) and has over 85 phytocannabinoids which can have a positive synergistic effect as compared to compositions having fewer cannabinoids. There may also be benefits to other components of it (e.g., terpenes). Such benefits and effect may include faster penetration and/or permeation of the therapeutic components thereof. Full spectrum hemp oil can include full spectrum hemp oil that has been purified to include less than the below stated amounts of one or more of the following impurities:

Aflatoxins B1, 82, G1, G2 (fats, oils, lecithin, egg powder): <0.1 µg/kg of each of Aflatoxin B1,
Aflatoxin B2, Aflatoxin G1 and Aflatoxin G2, Sum of all positive Aflatoxins<0.4 µg/kg.
GlyphosatelAMPAiGlufosinate: <0.1 mg/kg of each of Glufosinate, Glyphosate and
Aminomethylphosphonic acid (AMPA)
Mercury: <0.02 mg/kg
Arsentic: <0.03 mg/kg
Cadmium: <0.01 mg/kg
Lead: <0.05 mg/kg.

Embodiments of the present disclosure may also optionally include an effective amount of THC and other forms of THC such as THCA, THCV, delta-8 THC, delta-9 THC etc. Unit dosage formulations of the embodiments of the present disclosure can include THC in the amount of about 0.1 mg. to about 10 mg., about 1 mg. to about 10 mg., about 4 mg. to about 6 mg. about 5 mg. In addition to the other benefits that can be provided by other cannabinoids, THC may relieve stress and be a sleeping aid.

Menthol is an active agent and an organic compound that can be made synthetically or obtained from mint oils such as corn mint and peppermint. Medicinally, it been found that menthol can have anesthetic (e.g., local) by, for example, blocking nerve signal transmission) and counterirritant properties as well as anti-inflammatory properties (e.g., systemic and local) when administered to a patient. Furthermore, menthol is a vasodilator that can accelerate the transport of active in the circulatory system. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Menthol can be in an amount of about 0.1 wt % to about 20 wt %, about 0.1 wt % to about 10 wt %, about 1 wt % to about 20 wt %, about 0.1 wt % to about 14 wt %, about 0.1 wt % to about 1 wt %, about 2 wt % to about 9 wt % or about 0.62 wt %. Unit dosage formulations of the embodiments of the present disclosure can include menthol in the amount of about 1 mg. to about 20 mg., about 1 mg. to about 10 mg., about 1 mg. to about 4 mg., about 3 mg. to about 4 mg., about 5 mg. to about 7 mg., about 8 mg. to about 10 mg., about 4 mg. to about 8 mg. or about 5 mg. to about 7 mg. An effective amount of menthol includes an anesthetic, pain reducing (e.g., analgesic) or anti-inflammatory effective amount of menthol.

Menthol may be stabilized using methods know in the art, such as, for example, mixing it with about 0.1 wt % to about 10 wt %, about 0.5 wt % to about 5 wt % of a surfactant including edible nonionic surfactants and ionic surfactants, such as, for example, sucrose fatty acid ester, polysorbate (e.g., polysorbate 80), hydrogenated castor oil (e.g., polyoxyethylene hydrogenated castor oil), cocamidopropyl betaine, etc.

The aspects of the present disclosure also relate to embodiments including compositions, methods of making and methods of using included herein which also comprise the menthol component included in embodiments of the present disclosure in a stabilized menthol composition as well as methods of making and using them including a mixture of (a) menthol and (b) a menthol stabilizer compound including undecylenic acid methyl ester or undecylenic acid or a salt (preferably a pharmaceutically acceptable salt) thereof where the menthol in the stabilized menthol compositions is less susceptible to volatizing into a gas and remains in a form that can be administered in a composition in an amount closer to the amount originally included in the composition when formulated with less menthol volatizing away (i.e., lowering the rate of volatilization of the menthol from what it would be for menthol alone) from the original concentration and, thus, lowering the original concentration and diminishing the amount of the menthol originally added.

Undecylenic acid salts, including pharmaceutically acceptable salts may include, for example, inorganic acid addition, hydrochloride salts, sulfate and phosphate salts; and organic acid addition salts, such as alkyl sulfonate, arylsulfonate, acetate, maleate, fumarate, tartrate, citrate and lactate and metal salts including alkali metal salts, such as lithium salt, sodium salt and potassium salt and alkaline earth metal salts, such as magnesium salt and calcium salt, strontium salt, aluminum salt and zinc salt, and other multivalent salts such as for example, zirconium, iron, copper, silver, bismuth etc. Additionally primary secondary, and tertiary amine salts, organic and inorganic, mono and polyamines compounds could utilized. Examples include compounds such as urea, and amino acids such as lysine, histidine, arginine etc, could be utilized.

The stabilized menthol compositions can made by mixing together (a) menthol and (b) a menthol stabilizer compound in a ratio of (a) about 1 molar part menthol to (b) the amount of one or more than one of the menthol stabilizer compounds (undecylenic acid methyl ester, undecylenic acid or a salt of undecylenic acid, including mixtures thereof) of from about 0.005 molar part to about 1.00 molar part, about 0.010 molar part to about 0.750 molar part, about 0.020 molar part to about 0.50 molar part, about 0.050 molar part to about 0.250 molar part, or about 0.10 molar part. It is believed that the menthol stabilizer compounds (undecylenic acid methyl ester, undecylenic acid or a salt of undecylenic acid, including mixtures thereof) and menthol may associate to form a menthol analog where the menthol analog's vapor pressure becomes lower than menthol itself. As a result of having a lower vapor pressure, the menthol component of the menthol analog volatizes as a lower rate than menthol by itself.

One possible explanation for the stabilization of menthol by the compound of formula (I) may be that the menthol associates with the alkenyl side chain of the menthol stabilizer compounds (undecylenic acid methyl ester, undecylenic acid or a salt of undecylenic acid, including mixtures thereof) may provide a molecular attraction connecting the menthol stabilizer compounds (undecylenic acid methyl ester, undecylenic acid or a salt of undecylenic acid, including mixtures thereof) and a menthol molecule, such that more than one menthol molecule may associate with a molecule of one of the menthol stabilizer compounds (undecylenic acid methyl ester, undecylenic acid or a salt of undecylenic acid, including mixtures thereof).

The stabilized menthol compositions including menthol and at least one of the menthol stabilizer compounds (undecylenic acid methyl ester, undecylenic acid or a salt of undecylenic acid, including mixtures thereof) can be also be made first by dissolving menthol in a pharmaceutically acceptable suitable solvent such as, for example, as a low, medium, or long chain triglyceride. Examples of such solvents are coconut oil, olive oil, palm oil, hemp oil and castor oil. Still other acceptable solvents such as alcohols, ethers and polyalcohols, for example, propylene glycol, butylene glycol, and polyethylene glycols (PEGs) can also be used. The desired amount of at least one of the menthol stabilizer compounds (undecylenic acid methyl ester, undecylenic acid or a salt of undecylenic acid, including mixtures thereof) is then added to that mixture. Such compositions that include menthol, solvent and one or more than one of the menthol stabilizer compounds (undecylenic acid methyl ester, undecylenic acid or a salt of undecylenic acid, including mixtures thereof) may be made where the mixture of the these ingredients includes a molar ratio of about one molar part menthol to a range of from about 0.0050 molar part to about 1.00 molar part, about 0.010 molar part to about 0.750 molar part, about 0.020 molar part to about 0.50 molar part, about 0.050 molar part to about 0.250 molar part, or about 0.10 molar part of at least one of the menthol stabilizer compounds (undecylenic acid methyl ester, undecylenic acid or a salt of undecylenic acid, including mixtures thereof), preferably a molar ratio of about one molar part menthol to at most about 0.50 molar part, at most about 0.250 molar part or at most about 0.10 molar part of one or more than one of the menthol stabilizer compounds (undecylenic acid methyl ester, undecylenic acid or a salt of undecylenic acid, including mixtures thereof). Such mixtures of menthol, solvent and menthol stabilizer compounds (undecylenic acid methyl ester, undecylenic acid or a salt of undecylenic acid, including mixtures thereof) may be used when smaller amounts of menthol need to be stabilized (where the amount of menthol stabilizer compound (undecylenic acid methyl ester, undecylenic acid or a salt of undecylenic acid, including mixtures thereof) to be mixed with the menthol is so small that there isn't enough of it to dissolve the menthol).

Both menthol stabilized compositions (i.e., where the menthol is first dissolved in a solvent then dissolved in a menthol stabilizer compound (undecylenic acid methyl ester, undecylenic acid or a salt of undecylenic acid, including mixtures thereof) or where the menthol is directly dissolved in a menthol stabilizer compound (undecylenic acid methyl ester, undecylenic acid or a salt of undecylenic acid, including mixtures thereof)) can be used in orally administrated and non-orally administrated compositions (e.g., non-orally topically administrated compositions (e.g., place on the skin or other external tissues)). However, the menthol stabilizer compounds (undecylenic acid methyl ester, undecylenic acid or a salt of undecylenic acid, including mixtures thereof) can have a bitter taste. The dissolving of the menthol in solvent prior to the addition of at least one of the menthol stabilizer compounds (undecylenic acid methyl ester, undecylenic acid or a salt of undecylenic acid, including mixtures thereof) is preferably used in menthol containing therapeutic compositions to be administered orally because by first dissolving the menthol in a suitable solvent, less of the menthol stabilizer compounds (undecylenic acid methyl ester, undecylenic acid or a salt of undecylenic acid, including mixtures thereof) may be used, thus lessening the bitter taste of the menthol stabilized composition(undecylenic acid methyl ester, undecylenic acid or a salt of undecylenic acid, including mixtures thereof) and the final product in which it is included that is imparted by the menthol stabilizer compound (undecylenic acid methyl ester, undecylenic acid or a salt of undecylenic acid, including mixtures thereof).

Unit dosage formulations of the embodiments of the present disclosure may be prepared by the addition of about 2 mg. to about 20 mg., about 2 mg. to about 60 mg., about 5 mg. to about 30 mg., about 5 mg. to about 15 mg., about 15 mg. to about 30 mg. or about 30 mg. to about 45 mg. of cannabinoid. Unit dosage formulations of the embodiments of the present disclosure can include CBD in the amount of about 2 mg. to about 30 mg., 5 mg. to about 30 mg., about 5 mg. to about 15 mg. about 15 mg. to about 30 mg. or about 10 mg., for example, a phytocannabinoid, and about 1 mg. to about 20 mg., 1 mg. to about 15 mg., about 1 mg. to about 10 mg., about 1 mg. to about 4 mg., about 3 mg. to about 4 mg., about 5 mg. to about 7 mg., about 8 mg. to about 10 mg., about 4 mg. to about 8 mg. or about 5 mg. to about 7 mg, about 5 mg., about 10 mg., about 15 mg. or about 20 mg. of menthol.

The aspects of the present disclosure also relate to chewing gum and lozenge compositions, products and devices (e.g., chewing gum and lozenges including those that are unfilled and filled including liquid-filled or solid or semi-solid filled) for the delivery of, for example, pharmaceutical compositions, including analgesic pharmaceutical compositions, that contain a pharmaceutically effective amount of a pharmaceutically acceptable and effective cannabinoid and a pharmaceutically effective amount of menthol and oral care chewing gum and lozenge compositions, products and devices (e.g., chewing gum and lozenges including those that are unfilled and filled including liquid-filled or solid or semi-solid filled), including oral care analgesic chewing gum and lozenge compositions, products and devices (e.g., chewing gum and lozenges including those that are unfilled and filled including liquid-filled or solid or semi-solid filled), that contain a pharmaceutically effective amount of an oral or dental acceptable and effective cannabinoid and a pharmaceutically effective amount of menthol.

An embodiment of the present disclosure relates to chewing gum and lozenge compositions, products and devices (including those that are unfilled and filled including liquid-filled or solid or semi-solid filled chewing gum or lozenge) including a pharmaceutically effective amount of a pharmaceutically acceptable and effective cannabinoid, for example, a phytocannabinoid or full spectrum hemp oil, and a pharmaceutically effective amount of a pharmaceutically acceptable and effective menthol along with a pharmaceutically acceptable carrier.

An embodiment of the present disclosure relates to a filled chewing gum or lozenge including a chewing gum or lozenge base shell enclosing an internal void therein and a liquid filling in the void, the liquid filling and/or chewing gum or lozenge base shell including a pharmaceutically effective amount of a pharmaceutically acceptable and effective cannabinoid, for example, a phytocannabinoid or full spectrum hemp oil, and a pharmaceutically effective amount of a pharmaceutically acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pharmaceutically effective amount of an oral or dental acceptable and effective cannabinoid, for example, a phytocannabinoid or full spectrum hemp oil, and a pharmaceutically effective amount of an oral or dental acceptable and effective menthol along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including a pharmaceutically effective amount of an oral or dental acceptable and effective cannabinoid, for example, a phytocannabinoid or full spectrum hemp oil, and a pharmaceutically effective amount of an oral or dental acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pain reducing (e.g., analgesic and/or anesthetic) and/or anti-inflammatory pharmaceutically effective amount of a pharmaceutically acceptable and effective cannabinoid, for example, a phytocannabinoid or full spectrum hemp oil, and a pain reducing (e.g., analgesic and/or anesthetic) and/or anti-inflammatory pharmaceutically effective amount of a pharmaceutically acceptable and effective menthol along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including a pain reducing (e.g., analgesic and/or anesthetic) and/or anti-inflammatory pharmaceutically effective amount of pharmaceutically acceptable and effective cannabinoid, for example, a phytocannabinoid or full spectrum hemp oil, and a pain reducing (e.g., analgesic and/or anesthetic) and/or anti-inflammatory pharmaceutically effective amount of menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pain reducing (e.g., analgesic and/or anesthetic) and/or anti-inflammatory pharmaceutically effective amount of an oral or dental acceptable and effective cannabinoid, for example, a phytocannabinoid or full spectrum hemp oil, and a pain reducing (e.g., analgesic and/or anesthetic) and/or anti-inflammatory pharmaceutically effective amount of an oral or dental acceptable and effective menthol along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including a pain reducing (e.g., analgesic and/or anesthetic) and/or anti-inflammatory pharmaceutically effective amount of an oral or dental acceptable and effective cannabinoid, for example, a phytocannabinoid or full spectrum hemp oil, and a pain reducing (e.g., analgesic and/or anesthetic) and/or anti-inflammatory pharmaceutically effective amount of an oral or dental acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pain reducing (e.g., analgesic and/or anesthetic) and/or anti-inflammatory pharmaceutically effective amount of a pharmaceutically acceptable and effective cannabinoid, for example, a phytocannabinoid or full spectrum hemp oil, and a pain reducing (e.g., analgesic and/or anesthetic) and/or anti-inflammatory pharmaceutically effective amount of a pharmaceutically acceptable and effective menthol along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including a pain reducing (e.g., analgesic and/or anesthetic) and/or anti-inflammatory pharmaceutically effective amount of a pharmaceutically acceptable and effective cannabinoid, for example, a phytocannabinoid or full spectrum hemp oil, and a pain reducing (e.g., analgesic and/or anesthetic) and/or anti-inflammatory pharmaceutically effective amount of a pharmaceutically acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pain reducing (e.g., analgesic and/or anesthetic) and/or anti-inflammatory pharmaceutically effective amount of an oral or dental acceptable and effective cannabinoid, for example, a phytocannabinoid or full spectrum hemp oil, and a pain reducing (e.g., analgesic and/or anesthetic) and/or anti-inflammatory pharmaceutically effective amount of an oral or dental acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pain reducing (e.g., analgesic and/or anesthetic) and/or anti-inflammatory pharmaceutically effective amount of a pharmaceutically acceptable and effective cannabinoid, for example, a phytocannabinoid or full spectrum hemp oil, and a pain reducing (e.g., analgesic and/or anesthetic) and/or anti-inflammatory pharmaceutically effective amount of a pharmaceutically acceptable and effective menthol along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including a pain reducing (e.g., analgesic and/or anesthetic) and/or anti-inflammatory pharmaceutically effective amount of a pharmaceutically acceptable and effective cannabinoid, for example, a phytocannabinoid or full spectrum hemp oil, and a pain reducing (e.g., analgesic and/or anesthetic) and/or anti-inflammatory pharmaceutically effective amount of a pharmaceutically acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including a pain reducing (e.g., analgesic and/or anesthetic) and/or anti-inflammatory pharmaceutically effective amount of an oral or dental acceptable and effective cannabinoid, for example, a phytocannabinoid or full spectrum hemp oil, and a pain reducing (e.g., analgesic and/or anesthetic) and/or anti-inflammatory pharmaceutically effective amount of an oral or dental acceptable and effective menthol along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including a pain reducing (e.g., analgesic and/or anesthetic) and/or anti-inflammatory pharmaceutically effective amount of an oral or dental acceptable and effective cannabinoid, for example, a phytocannabinoid or full spectrum hemp oil, and a pain reducing (e.g., analgesic and/or anesthetic) and/or anti-inflammatory pharmaceutically effective amount of an oral or dental acceptable and effective menthol along with a pharmaceutically acceptable carrier.

Another embodiment of the present disclosure relates to a filled chewing gum or lozenge including a chewing gum or lozenge base shell enclosing an internal void therein and a liquid filling in the void, the liquid filling and/or chewing gum or lozenge base shell including cannabinoid, for example, CBD or full spectrum hemp oil, in an amount of about 0.1 wt % to about 20 wt %, about 0.1 wt % to about 10 wt % or about 0.5 wt % to about 5 wt % and menthol in an amount of about 0.1 wt % to about 20 wt %, about 0.1 wt % to about 1 wt %, about 0.1 wt % to about 10 wt %, about 1 wt % to about 20 wt %, about 0.1 wt % to about 14 wt %, about 0.1 wt % to about 1 wt % or about 2 wt % to about 9 wt % along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including cannabinoid, for example, CBD or full spectrum hemp oil, in an amount of about 0.1 wt % to about 20 wt %, about 0.1 wt % to about 10 wt % or about 0.5 wt % to about 5 wt % and menthol in an amount of about 0.1 wt % to about 20 wt %, about 0.1 wt % to about 1 wt %, about 5 wt % to about 20 wt %, about 1 wt % to about 15 wt %, about 7.5 wt % to about 20 wt %, about 5 wt %, about 7.5 wt %, about 10 wt % or about 20 wt % along with a pharmaceutically acceptable carrier.

In another embodiment of the present disclosure, the a filled chewing gum or lozenge including a chewing gum or lozenge base shell enclosing an internal void therein and a liquid filling in the void, the liquid filling and/or chewing gum or lozenge base shell including cannabinoid, for example, phytocannabinoids or full spectrum hemp oil, in an amount of about 0.1 wt % to about 20 wt %, 0.1 wt % to about 1 wt %, about 0.1 wt % to about 10 wt % or about 0.5 wt % to about 5 wt %; and menthol in an amount of about 0.1 wt % to about 20 wt %, about 1 wt % to about 20 wt %, about 0.1 wt % to about 14 wt %, about 0.1 wt % to about 1 wt % or about 2 wt % to about 9 wt %, along with a pharmaceutically acceptable carrier.

An embodiment of the present disclosure relates to chewing gum and lozenge compositions, products and devices (including those that are unfilled and filled including liquid-filled or solid or semi-solid filled chewing gum or lozenge) including cannabinoid, for example, phytocannabinoids or full spectrum hemp oil, in an amount of about 0.1 wt % to about 20 wt %, 0.1 wt % to about 1 wt %, about 0.1 wt % to about 10 wt % or about 0.5 wt % to about 5 wt %; and menthol in an amount of about 0.1 wt % to about 20 wt %, about 0.1 wt % to about 10 wt %, 0.1 wt % to about 1 wt %, about 5 wt % to about 20 wt %, about 1 wt % to about 15 wt %, about 7.5 wt % to about 20 wt %, about 5 wt %, about 7.5 wt %, about 10 wt % or about 20 wt %, along with a pharmaceutically acceptable carrier.

A "pharmaceutically acceptable carrier" can include gum or lozenge base materials and known fill and filling compositions disclosed herein as well as those known in the art.

Hemp oil can contain about 25% CBD, hemp oil breakdown w/w %: phytocannabinoids=about 5.70%, CBD=about 1.9% Total about 7.60%. Unit dose weight is about 0.55 grams/dose and will deliver about 10 mg. CBD, about 30 mg. phytocannabinoids and about 0.08 mg. THC (negligible). Phytocannabinoids comprise the following: as of 2016, there are 11 subclasses: (1) cannabigerol (CBG); (4) cannabichromene (CBC); (5) cannabinol (CBD); (7) cannabicyclol (CBL); (8) cannabinodiol (CBND); (9) cannabielsoin (CBE); (10) cannabitriol (CBT); and (11) miscellaneous types.

All of the embodiments included here are with the proviso that the sum of ingredients in the exemplary compositions does not exceed 100%.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a subject.

In a further embodiment, a kit is disclosed. One example of such a kit is a kit including a composition or unit dose composition of one of the embodiments of the present disclosure including multiple unit doses and instructions for use.

These and other aspects and advantages of the exemplary embodiments will become apparent from the detailed description. Additional aspects and advantages of the present disclosure will be set forth in the description that follows, and in part will be obvious from the description, or may be learned by practice of the present disclosure. Moreover, the aspects and advantages of the present disclosure may be realized and obtained by means of the instrumentalities and combinations particularly pointed out in the appended claims.

Optional ingredients include anti-oxidants, colorants, flavorings and flavor enhancers, preservatives, salivary stimulating agents, cooling agents, co-solvents (including oils), emollients, bulking agents, anti-foaming agents, surfactants, sweetening agents, fillers and taste-masking agents.

Sweetening agents, including pharmaceutically acceptable sweetening agents and sugar-free sweetening agents, can include, for example, saccharin, dextrose, sucrose, lactose, maltose, levulose, aspartame, *Stevia* (e.g., *Stevia rebaudiana* leaf/stem extract), sodium cyclamate, D-tryptophan, dihydrochalcones, acesulfame, monk fruit sweeteners and mixtures thereof. Sweetening agents can be generally used at levels of from about 0.005 wt % to about 5 wt %, by weight of the composition, preferably from about 2 wt % to about 3 wt %.

Fillers, including pharmaceutically acceptable fillers, can include, for example, fumed silica, calcium carbonate, talc, corns starch, clays, methacrylate powder, polyethylene/polypropylene beads, etc. Fillers can be generally used at levels of from about 15 wt % to about 40 wt %, by weight of the composition, preferably from about 20 wt % to about 30 wt %.

Another optional ingredient can be a saliva stimulant. Exemplary saliva stimulants include, but are not limited to, acidic compounds as citric acid, malic acid, lactic acid, ascorbic acid and tartaric acid. In other embodiments, some sweeteners can be used as saliva stimulants, including but not limited to glucose, fructose, xylose, maltose, and lactose. In certain embodiments, a saliva stimulant (e.g., citric acid) can be in an amount of from about 0.1 wt % to about 10 wt %, 0.1 wt % to about 7%, 0.1% to about 6% or about 2% to about 6%. A unit dose of a saliva stimulant (e.g., citric acid) can be in an amount of from about 10 mg. to about 70 mg. A saliva stimulant may activate the salivary gland, replenish the salivary flow and, thereby, to promote a faster disintegration of the chewing gum, lozenge or the contents (e.g., liquid-filling) thereof and its components and increase the speed with which the actives are administered.

Embodiments of the present disclosure may be delivered for local or systemic administration to an oral cavity surface, for example, an oral mucous membrane or cheek tissue in the oral cavity, in active agent-transmitting relation thereto, for example, chewing, sucking on or biting and breaking the chewing gum or lozenge composition, the active agents being cannabinoid, for example, phytocannabinoid or full spectrum hemp oil, and menthol.

Alternatively, the chewing gum and lozenge compositions (e.g., chewing gum and lozenges including those that are unfilled and filled including liquid-filled or solid or semi-solid filled liquid-filled) compositions, products and devices of the present disclosure include an active agent reservoir within the interior of such a system, the active agents present in a pharmaceutically acceptable liquid vehicle or carrier, e.g., an aqueous vehicle or carrier. In such embodiments including a reservoir, the cannabinoid, for example, CBD or full spectrum hemp oil, and menthol could be in the reservoir that is surrounded by a shell of gum base material.

Embodiments of the present disclosure may be formulated to be immediate and/or modified release. Modified release formulations include delayed-, sustained-, pulsed-, controlled, targeted and programmed release.

Suitable modified release formulations for the purposes of the present disclosure may be adapted, for example, from those described in U.S. Pat. No. 6,106,864. Details of other suitable release technologies such as, for example, high energy dispersions and osmotic and coated particles are to be found in Pharmaceutical Technology On-line, 25(2), 1-14, by Verma et al (2001). The use of chewing gum to achieve controlled release may be adapted from those described in WO 00/35298.

Other embodiments of the present disclosure include a method of relieving pain and/or inflammation or for nutritional benefit by administering to the oral cavity of a mammal in need of such treatment at least one of the compositions disclosed herein. Still other embodiments of the present disclosure include a method of relieving mouth, oral or dental pain by topically administering to the oral cavity of a mammal in need of such treatment at least one of the compositions disclosed herein. Still other embodiments of the present disclosure include a method of relieving pain and/or inflammation by administering to the oral cavity of a mammal in need of such treatment at least one of the compositions disclosed herein to a tooth, teeth or other oral tissues or surfaces. Still other embodiments of the present disclosure include a method of relieving mouth, oral or dental pain and/or inflammation by topically administering to the oral cavity of a mammal in need of such treatment at least one of the compositions disclosed herein to a tooth, teeth or other oral tissues or surfaces.

For embodiments that are placed within the oral cavity for chewing, sucking and/or biting therein, the dosing time can range from about 5 minutes to about 15 minutes, about 5 minutes to about 10 minutes (based on in vitro testing), 5 minutes to about 7 minutes or about 7 minutes. The remainder can then be removed from the oral cavity or chewed and swallowed to pass through the digestive system for removal.

Formulations suitable for oral administration include solid, semi-solid and liquid systems such as soft or hard capsules containing multi- or nano-particulates, liquids, or powders; unfilled or filled lozenges (including liquid-filled filled or solid or semi-solid filled); unfilled or filled chewing gum (including liquid-filled or solid or semi-solid filled).

The amount of the active agent administered will be dependent on the subject being treated, the severity of the disorder or condition, the rate of administration, the disposition of the compound and the discretion of the prescribing physician. However, an effective dosage is in the range of about 0.001 to about 100 mg. per kg body weight per day, preferably about 1 to about 35 mg./kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of an active agent together with an at least one additional pharmaceutical or medicinal agent, either sequentially or simultaneously.

The present disclosure includes the use of a combination of an active agent and one or more additional pharmaceutically active agent(s). If a combination of active agents is administered, then they may be administered sequentially or simultaneously, in separate dosage forms or combined in a single dosage form. Accordingly, the present disclosure also includes pharmaceutical compositions comprising an amount of: (a) a first agent comprising an active agent or a pharmaceutically acceptable salt of the compound; (b) a second pharmaceutically active agent; and (c) a pharmaceutically acceptable carrier, vehicle or diluent.

The compositions of the present disclosure may also serve to deliver an active agent using other routes of administration. For example, the compositions may be formulated with excipients, carriers and the like suitable for oral administration of an orally active drug.

For filled gum and lozenge embodiments, the outside gum or lozenge base shell can range is about 75% to about 99.00 wt % and the center can range from about 1.00 wt % to about 10.00 wt %. The outside gum or lozenge base shell weight can range from about 4.0 grams to about 25.0 grams. The liquid center weight can range from about 0.5 grams to about 6.0 grams with about 5.0 grams being preferred.

Embodiments of the present disclosure may also optionally include an effective amount of THC. Unit dosage formulations of the embodiments of the present disclosure can include THC in the amount of about 0.1 mg. to about 10 mg., about 1 mg. to about 10 mg., about 4 mg. to about 6 mg. about 5 mg. In addition to the other benefits that can be provided by other cannabinoids, THC may relieve stress and be a sleeping aid. In embodiments of the present disclosure in which there is both THC and CBD or full spectrum hemp oil, because CBD or full spectrum hemp oil may have an ameliorating anti-oxidating effect on THC when mixed together, then the CBD or full spectrum hemp oil may be located in a separate part (shell or filling) from the THC component, such as CBD or full spectrum hemp oil in the outer portion to allow for faster absorption so as not to interfere with the THC component.

The present disclosure is directed to a method and product which provides functional components such as, herbal, medicinal and/or vitamin substances for various applications (e.g., weight control substances) to an individual other than through the consumption of pills, suppositories, diet beverages and/or tasteless and low caloric foodstuffs. In one embodiment, the present disclosure is directed to a particular gum product having at its center a composition different from the surrounding gum and having distinct functional and metabolic characteristics. For example, various metabolism increasing components can be provided in the interior of a gum in a liquid or semi-liquid form while the gum itself can be of a traditional gum composition and/or may incorporate various other desirable metabolic increasing components to supplement and/or co-act with components contained in the liquid center of the gum. Indeed, in one particular embodiment of the present disclosure, time release capsules may be provided suspended in a liquid medium inside a gum enclosure.

The present disclosure also pertains to a gum/lozenge/lollipop (e.g., lozenge on a stick), but the present disclosure is not so limited and includes one or more combinations of ingredients as set forth, for example, in Tables I and II below, which may be useful in numerous and varied applications. For illustration purposes only, however, the following discusses weight loss applications of the present disclosure in combination with other features and components of the present disclosure. In one embodiment, chewing of the gum-based product releases the interior liquid substance, thus providing a product and a method desirable by weight conscious individuals who do not wish to publicly announce or disclose their dietary desires. In a preferred embodiment, the substance contained within the gum (e.g. the interior liquid substance) would have as a principal characteristic the capability of increasing a user's caloric burn rate (e.g. by increasing a person's metabolism, adjusting/regulating hormonal activity in an individual, providing fiber to increase a person's feelings of satiety).

In a particular embodiment of the present disclosure, a chewing gum can be utilized having liquid interior components surrounded by the dense gum, for example, the interior can have a density less than 10% as dense as the exterior gum, more preferably at least about 15% less dense, and more preferably, at least about 35% less dense than the surrounding gum. The interior liquid components, in addition to those also included in the present disclosure, can be herbal, organic, natural, chemical and/or hormonal in nature, and may be selected dependent upon their individual and synergistic characteristics, with the objective being to increase a person's metabolism in order to achieve a higher caloric burn rate and/or to decrease the desire for additional food (e.g. generate a feeling of satiety or fullness). It is within the scope of the present disclosure to incorporate various known diet control substances in either the gum base material itself and/or in the liquid interior material encompassed by the gum base material. In a preferred embodiment, however, the surrounding gum base material can be comprised of traditional gum flavors and compositions and the interior liquid and/or semi-liquid (e.g. gel) components of the present disclosure comprise diet regulating substances.

Yet another embodiment of the present disclosure can relate to a hard candy substance (e.g. primarily comprising a natural sugar and corn syrup base) often referred to as a "lozenge," "sucker" or "lollipop." The interior of the lozenge, sucker or lollipop, however, contains a less rigid, soft and/or liquid or semi-liquid component. The enclosed material of the lollipop includes metabolic enhancers for weight and caloric control.

In still another embodiment, a lozenge can be manufactured having a denser exterior and a less dense interior, where either the interior or exterior of the lozenge, or both, can contain diet controlling substances. Preferably, diet controlling substances can be positioned within the interior of such lozenges so as to facilitate the enjoyment by an individual of consuming the lozenge without the possible unpleasant and/or undesirable taste characteristics of various dietary components within the center of the lozenge.

It will be understood that one purpose of certain embodiments of the present disclosure can be to increase metabolic efficiency and to burn calories in an individual. Herbal additives may be incorporated into such products to aid in the body's ability to digest food and/or to block absorption of fat molecules into the system. For example, chitosan compositions can be utilized either in the interior and/or exterior of the gum, lollipop and lozenge embodiments desired above and hereafter. In addition to chitosan, other fiber-like components, vitamins and minerals (e.g., especially calcium compositions to treat osteoporosis) can be incorporated into the embodiments of the present disclosure to provide desired feelings of satiety or fullness to an individual using such products and/or to treat various vitamin and/or mineral deficiencies.

While portions of the present disclosure is directed to administering diet control substances to individuals, it should be understood that other medicinal and/or nutritional and/or biological components can be administered to animals in general (companion pets, livestock, etc.) but preferably humans. Indeed, the present inventor believes that the administration of medicinal compounds to young children can be greatly facilitated by use of the embodiments of the present disclosure given that children are more apt to take medicine in the for of a lollipop, lozenge or gum, particularly if the taste and flavor and textural characteristics of such candy products are preserved and effective amounts of desired components are delivered to such individuals when consuming such products.

TABLE I

The following contains a list of other possible components that may be incorporated into the center of the chewing gum, lollipop and lozenge aspects of the present disclosure:

Dexatrim
Chitosan
Oatmeal fiber
Vitamins
Mineral supplements
Medicinal components
Lipid substances (HDLs)
Chemotherapeutic agents
Diuretics
Antacids
Antibiotics
Herbal components
Stimulants
Metabolic enhancers The following U.S. issued patents are also incorporated herein by reference: U.S. Pat. No. 5,474,989 by Hasimoto et al., U.S. Pat. No. 5,747,475 by Norquist et al., U.S. Pat. No. 5,830,883 by Block et al., U.S. Pat. No. 5,880,109 by Nakamura et al., U.S. Pat. No. 4,963,367 by Ecanow, U.S.

Pat. No. 4,738,850 by Thakur et al., U.S. Pat. No. 5,846,952 by Vournakis et al., and U.S. Pat. No. 4,223,023 by Furda. Support for various active ingredients being included in chewing gum formulations as encompassed by the present disclosure can be found in the above-referenced incorporated by reference patents, including, but not limited to the inclusion of vitamin B6 and vitamin B12. It will therefore be appreciated by one of skill in the art that various compositions, formulations, masking agents (e.g., to "mask" unpleasant flavors and/or textures and/or mouth feel characteristics of vitamins, medicinal compounds, minerals, etc.) and binders can be combined with the present structure of embodiments of the present disclosure to achieve various desired purposes. For example, controlled release formulations are encompassed by the present disclosure (including use of microencapsulation of one or more of the ingredients) as are the preparation and use of various different carrier vehicles useful for medicinally administering compositions to animals, time release formulations, compositions having desirable solubility and dissolution rates, and the incorporation into embodiments of the present disclosure of food additives such as vitamins, pharmaceutical preparations and other compounds, specifically those that reduce the absorption of lipids such a chitosan.

Both the gum with liquid-type fillers and the lollipop with a gum-based center can be comprised of one or more of the following: xanthan, guar, locust bean gum, karaya, gum tragacanth, carrageenans, alginates, gum arabic, corn syrup, sugar, starches, gum bases. While multiple recipes exist, most candy substances can also be made from natural and herbal substitutes listed in Table II. The cavities that are extruded in both the gum and the lollipop can be made with one or more cavities that can be filled with multiple bio-enhancing and weight management substances, compiling all or some of the properties in Table II. The combination of them will achieve various results. Example: Guarana and malluang and chitosan will create energy and a feeling of "fullness" for the consumer; chromium picolinate (RE. 33, 988) and ginseng and ginger will allow the user to burn calories more efficiently).

TABLE II

| | |
|---|---|
| Siberian Ginseng | Vitamin E |
| Green Tea | Zinc |
| Casgara Sagrada | Mahuang |
| Apple Pectin | *Astragalus* |
| Dandelion | Guarana |
| Chickweek | Bee Pollen |
| *Gymnema sylvestre* | Chromium Picolinate |
| Licorice | Bluegreen Algae |
| Bladderwrack | Royal Jelly |
| Ginger | Damiana |
| Magnesium | Lecithin |
| Sarsaparilla | Gotu Kola |
| Golden Seal | Nettles |
| Chitosan | |

The amounts of all or some of these ingredients can vary, preferably being present in an amount between no less than about 0.05 mg. The size of the gum exterior can be made of a size less than 4.5 grams to more than 18.4 grams with the cavity center being able to accommodate a volume between 0.5 mg to more than 5 grams. The lollipop or lozenge can be a total size of less than 0.65 oz. with the cavity center being a volume of no more than 0.42 oz. and no less than 4.5 grams, to a size larger than 1.35 oz. with a cavity center being of at least 19 grams.

Other embodiments of the present disclosure can also include a beverage, so-called a Bloody Mary beverage, that includes the following: in a 12 fluid once serving: up to but not exceeding 9.9% alcohol (by volume); no fat; up to 1200 mg of sodium; 3 grams of protein; Vitamin C, Vitamin A, calcium, potassium and iron. In a preferred embodiment the beverage includes water, tomato concentrate, natural grain spirits, high fructose corn syrup, aloe vera juice, sodium chloride, vinegar, citric acid, taurine, pectin, ascorbic acid, and citrus aurantium extract. In still other embodiments, the beverage includes the following: fresh horseradish, tomato juice, Tabasco, worcestershire sauce, celery salt, and one of amontillado; cream sherry, and pure cane sugar. Another embodiment of the present disclosure includes a beverage consisting of: water; a tomato concentrate having a tomato soluble solids content of about 24% to about 36% by weight, ethyl alcohol, Vitamin C, Vitamin A, calcium, potassium, iron, water, high fructose corn syrup, aloe vera juice, sodium chloride, vinegar, citric acid; taurine, pectin, ascorbic acid, and citrus aurantium extract, horseradish, worcestershire sauce, and celery salt. Certain other embodiments are directed to compositions that have the benefits of an energy drink, and include at least the following: tomato juice containing lycopene, Ginger, Honey, taurine and caffeine. By way of providing additional background, context, and to further satisfy the written description requirements of 35 U.S.C. § 112, the following references are incorporated by reference in their entireties: U.S. Patent Publication No. 20130115329 to Savant, et al. and U.S. Pat. No. 8,202,561 to Livaich. One of skill in the art will further appreciate that the beverage ingredients of the above can also be incorporated into the chewing gum and lollipop embodiments as further described herein.

Incorporated by reference in its entirety are the following U.S. patents directed generally to chewing gum compositions, methods and apparatus for making chewing gum, and in particular, methods for enabling one of skill in the art to produce soft-centered chewing gums as contemplated by the present disclosure. One aspect of the embodiments of the present disclosure, however, should be understood as being distinguished from such prior art references and such incorporation by reference is only provided for enabling support of the numerous ways in which the particular novel product can be manufactured. The U.S. patents incorporated by reference are as follows: U.S. Pat. Nos. 5,922,347; 5,916,606; 5,912,030; 5,900,230; 5,885,630; 5,866,179; 5,858,423; 5,846,557; 5,834,002; 5,827,526; 5,824,291; 5,736,175; 4,156,740; 5,498,429; 4,466,983; 4,157,402; 5,569,477; 5,125,819; 5,248,508; 4,975,288; 4,792,453; 4,980,178; 4,683,138; 5,087,460; 4,292,329; 4,642,235; 4,316,915; 4,513,012; 4,250,196; 5,431,929; and 4,647,450.

An embodiment of the present disclosure includes a chewing gum consisting essentially of a first substance configured so as to have at least one cavity retaining a liquid or semi-liquid substance as a second substance, wherein at least said first substance has active ingredients consisting essentially of riboflavin, vitamin B6, vitamin B 12, niacin, caffeine, BHT, xylitol, maltitol, citric acid, sucralose, and a metabolic enhancer, said active ingredients together present in an amount of at least about 0.05 mg and up to 5 grams. The active ingredients can be present in a controlled release formulation and/or microencapsulated.

Another embodiment of the present disclosure includes a chewing gum consisting essentially of a first substance configured so as to have at least one cavity retaining a liquid or semi-liquid substance as a second substance, wherein at least said second substance has active ingredients consisting essentially of riboflavin, vitamin B6, vitamin B12, vitamin B3, and a metabolic enhancer, said active ingredients together present in an amount of at least about 0.05 mg and up to 5 grams. The active ingredients can be present in a controlled release formulation and/or microencapsulated.

An embodiment of the present disclosure includes a chewing gum consisting essentially of a first substance configured so as to have at least one cavity retaining a liquid or semi-liquid substance as a second substance, wherein at least said second substance has active ingredients consisting essentially of guarana, a metabolic enhancer that increases a user's metabolism in order to achieve a higher caloric burn rate, riboflavin, vitamin B6, vitamin B 12, and niacin, said active ingredients together present in an amount of at least about 0.05 mg and up to 5 grams. The active ingredients can be present in a controlled release formulation and/or microencapsulated.

There are various chewing gum and lozenge base shell formulations as well as formulations of the filling, e.g., liquid fillings, that are known and can be used in the embodiments of the present disclosure as well as know methods of making such embodiments.

Such center-filled chewing gums typically consist of a gum base shell and a center fill composition comprising one or more carbohydrate syrups, glycerine, thickeners, flavors, acidulants, colors, sugars and sugar alcohols as well as other ingredients included in embodiments of the present disclosure.

An example, the chewable gum base shell enclosing the center fill may be any chewable gum base in conventional amounts ranging from about 18% to about 99% by weight of the gum base shell. The gum base shell may comprise a sweet, water-soluble bulking agent. For sugar gums, the bulking agent may comprise dextrose, sucrose, maltose, dextrin, dried invert sugar, fructose, levulose, galactose, corn syrup or corn syrup solids or combinations thereof. For sugarless gums, the bulking agent may comprise sugar alcohols such as sorbitol, mannitol, xylitol, or combinations thereof. The bulking agent typically comprises from about 30% to about 80% by weight of the gum base shell.

Other typical examples of the ingredients found in this chewing gum base may include masticatory substances of vegetable origin, such as chicle, crown gum, nispero, rosidinha, jelutong, pendare, perillo, niger gutta, tunu, etc., masticatory substances of synthetic origin, such as butadiene-styrene polymer, isobutylene-isoprene copolymer, petroleum wax, polyethylene, polyisobutylene, polyvinylacetate, etc., plasticizers, such as lanolin, stearic acid, sodium stearate, potassium stearate, etc., antioxidants, such as, butylated hydroxyanisole, butylated hydroxytoluene, and propyl gallate. This chewing gum base may contain a sugar sweetener or non-sugar sweetener as described above with respect to the center fill. Where present, the natural sugar or sugar alcohol may be employed in an amount ranging from about 90 to about 0.05% by weight of the gum. This chewing gum base may also contain conventional ester gums, polydextrose, fillers, such as calcium carbonate, and texturizers, such as hydrated alumina, plasticizers, softeners or emulsifiers, such as lecithin, fatty acids, glycerine, glyceryl monostearate, hydrogenated vegetable oils, sorbitan monostearate, tallow, propylene glycol, F. D. &C. coloring agents, and other conventional chewing gum additives as will be apparent to those skilled in the art.

Conventional flavors such as liquid or spray-dried flavors may also be incorporated in the gum base (e.g., used as a shell) in amounts determined by preference, but preferably constituting about 1% by weight of the gum shell. The gum base (e.g., used as a shell) may also comprise a coloring agent in a conventional amount of about 0.1% to about 2.0% by weight of the shell and a plasticizing agent in an amount constituting about 0.1% to about 25% by weight of the gum shell.

The chewing gum base composition that can be used in the shell portion can be manufactured in a conventional known manner. For example, first, the base is heated and placed in a running mixer. If coloring is desired it may be added at this point followed by the bulking agent, the plasticizing agent and flavor. When the chewing gum is removed from the mixer it is combined with the center fill using conventional product-forming equipment in a known manner. Such product-forming equipment preferably includes an extruder (such as a Weisert, Loser & Sohn Model KE4); a sizer (such as a Hansella Model 165A); a Uniplast machine (such as a Hansella Model 160C); and a cooling tunnel (such as a Hansella Model 170B); because the nature and operations of such equipment are well-known in the art.

For lozenge embodiments, a lozenge can include a known candy shell (also referred to herein as a "lozenge base shell"), for example, a shell of a suitable sugar base for a hard candy shell, including from about 30% to about 85% glucose syrup and from about 15% to about 70% sucrose. Alternatively, a sugar-free base can be used for the shell. Suitable sugar-free bases include bulk sweeteners such as isomalt, maltitol and sorbitol. Isomalt and maltitol are preferred. The inner surface of the shell can also have a separate edible lining to prevent or reduce interaction of the filling with the shell.

The center fill of the chewing gum and lozenge embodiments of the present disclosure, in addition to the other ingredients included above (e.g., full spectrum hemp oil, menthol, etc.) may comprise one or more carbohydrate syrups, glycerine, thickeners, flavors, acidulants, colors, sugars and sugar alcohols in conventional amounts; the ingredients are combined in a conventional manner. The center fill preferably can include, for example, from about 1% to about 40% by weight of the chewing gum or lozenge. One embodiment of the center filled lozenge can include chewing gum base material as the center filling. The lozenge can include from 60 to 95%, preferably from 75 to 85%, of a candy shell and from 5 to 40%, preferably from 15 to 25%, of a filling, by weight of the lozenge.

An emulsifier may also be present in the filling. The emulsifier can be a food-grade material. Suitable emulsifiers include mono-and di fatty acid glycerides such as those based on soya oil e.g. Imwitor 440 from Huels, acetoglycerides such as Dynacet 211, monoglycerides esterified with citric acid, such as Imwitor 370, and lecithins such as the Topicithin range from Lucas Meyer, Germany. Suitable levels of the emulsifier can be from 0.001 to about 1%, more preferably from about 0.005 to about 0.1% and especially from about 0.01 to about 0.05% by weight of the filling.

In embodiments of the present disclosure, the menthol and cannabinoid, for example, full spectrum hemp oil may be mixed together and used as the fill (along with other desired syrup or liquid components included herein), the shell (either gum or lozenge) or both. Alternatively, the fill or the shell can include one of the menthol and cannabinoid, for example, full spectrum hemp oil. Embodiments of the present disclosure where there is a shell and fill material, these are filled chewing gum or lozenges.

For those embodiments of the present disclosure where there is only lozenge candy material or gum base material, the menthol and cannabinoid, for example, full spectrum hemp oil are included those lozenge candy material or gum base material. Embodiments of the present disclosure where there is only lozenge candy or gum base without filing, these are unfilled chewing gum or lozenges.

Centre-filled lozenges such as those included in the present disclosure can be manufactured by deposit, rope-forming and extrusion processes as known in the art. Extrusion and rope-forming processes are preferred. An example of an extrusion process is described in U.S. Pat. No. 5,458,894. An example of an extrusion process is described in U.S. Pat. No. 5,002,791.

The lozenges of the present disclosure can also be prepared using a variety of known processing technologies including double depositing, hand-pressing, rotary forming and extrusion. Such techniques are well known in the art such as disclosed in Sugar Confectionery Manufacture, $2^{nd}$ Edition, Edited by E. B. Jackson (1995), incorporated herein by reference for all purposes in its entirety. In an embodiment of the present disclosure, the lozenges of the present disclosure can be made by separately combining the ingredients of the shell and the core in a vessel and then delivering a stream of the respective materials to a manifold which provides for the interruptible flow of the core ingredients and a continuous flow of the shell ingredients surrounding the core. The resulting product is ejected in discrete units corresponding to the desired weight and size of the confectionery product and placed in trays with individual compartments for storing the confectionery products until they cool to ambient temperature.

In one embodiment of the present disclosure, the core fill component ingredients are degassed. Degassing techniques remove air from the core material thus at least minimizing chemical reactions therein. The core can be prepared in an enclosed mixing vessel and processed under vacuum. Alternatively, the core fill component ingredients are combined and mixed together and then a vacuum is applied to the mixture to remove any gases contained therein.

The center-fill gum of the present disclsoure may be formed by techniques known in the art which includes the method described by U.S. Pat. No. 6,280,780 to Degady et al. ("Degady") which is herein incorporated by reference in its entirety. Degady describes an apparatus and method for forming center-filled gum pellets. The method includes first extruding a liquid-filled rope of a chewing gum layer and passing the rope through a sizing mechanism including a series of pairs of pulley-shaped roller members. The roller members "size" the rope or strand of gum material such that it leaves the series of rollers with the desired size and shape for entering a tablet-forming mechanism.

The rope is then led into a tablet-forming mechanism including a pair of rotating chain die members which are endless chain mechanisms and both rotate at the same speed by a motor and gear mechanism. Each of the chain mechanisms include a plurality of open curved die groove members which mate and form die cavities in which the pieces of gum material (pellets or tablets) are formed. While Degady is limited to the formation of pellet or tablet shaped pieces, the gum pieces may be of other shapes as described above. The shape of the die groove members may be altered to provide any desired shape.

The shapes and sizes of the chewing gum or lozenge can be as exemplified in FIGS. 1-8 or can be any other three-dimensional shape such as, for example, polygons (e.g., having a cross-sectional shape of a rectangle, square, pentagon, hexagon, etc. or cubes, spheres, ellipses, etc.).

Figure 1B:
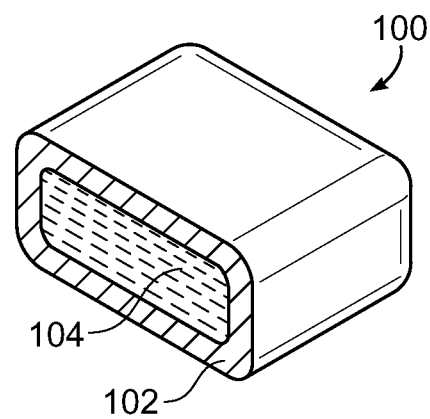
FIG. 1B is illustrative of a cross-section view of the exemplary center-filled chewing gum embodiment of FIG. 1A.

An exemplified embodiment of the present disclosure is illustrated in FIGS. 1A and 1B. FIG. 1A is an exterior view of and FIG. 1B is a cross-section view that illustrate an example of a center-filled chewing gum 100 including a shell of gum base 102 and filling material 104. The filling material 104 can be filling material included in the present disclosure or those know in the art. The piece of center-filled chewing gum 100 can be formed using known techniques and methods including those included in the present disclosure.

Figure 2:
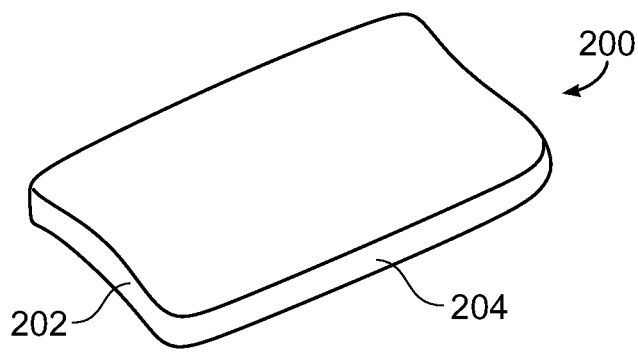
FIG. 2 is illustrative of an exterior perspective view of an exemplary cut and wrap chewing gum embodiment of the present disclosure.

Another exemplified embodiment of the present disclosure is illustrated in FIG. 2. FIG. 2 is an example of a cut and wrap chewing gum 200 that includes gum base in the piece of the cut and wrap chewing gum 200. The piece of the cut and wrap chewing gum 200 can be formed using known techniques and methods including passing the gum base through a die the shape of sides 202 or 204, cutting the extruded gum base once the desired size has exited the die and wrapping the cut piece.

Figure 3:
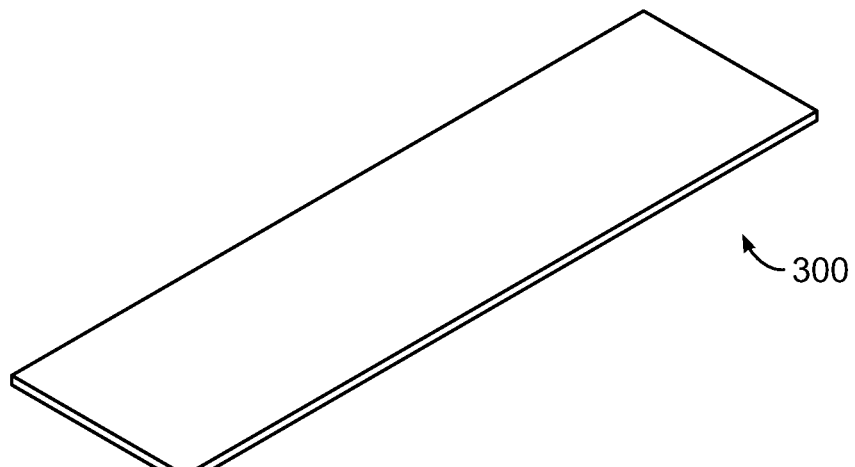
FIG. 3 is illustrative of an exterior perspective view of an exemplary stick or tab chewing gum embodiment of the present disclosure.

Another exemplified embodiment of the present disclosure is illustrated in FIG. 3. FIG. 3 is an example of a stick or tab chewing gum 300 that includes gum base in the piece of the stick or tab chewing gum 300. The piece of the stick or tab chewing gum 300 can be formed using known techniques and methods including passing a portion of the gum base through a pair of rollers to produce an elongated and thin form, cutting the elongated and thin form of the gum base once the desired size has exited the rollers and wrapping the cut piece.

Figure 4A:
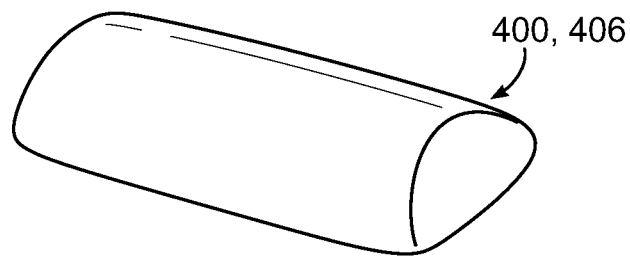
FIG. 4A is illustrative of an exterior perspective view of an exemplary pillow or pellet piece of chewing gum embodiment of the present disclosure.
Figure 4B:
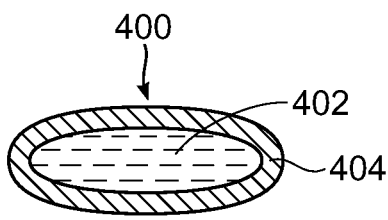
FIG. 4B is illustrative of a cross-section view of one embodiment of an exemplary pillow or pellet piece of chewing gum embodiment with an exterior illustrated in FIG. 4A.
Figure 4C:
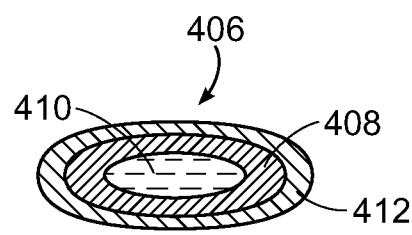
FIG. 4C is illustrative of a cross-section view of another embodiment of an exemplary pillow or pellet piece of chewing gum embodiment with an exterior illustrated in FIG. 4A.

Another exemplified embodiment of the present disclosure is illustrated in FIGS. 4A-4C. FIG. 4A is an exterior view of examples of a pillow or pellet piece of chewing gum shown in cross-section in FIGS. 4B and 4C. Pillow or pellet 400 includes gum base 402 and an exterior coating 404. Pillow or pellet 406 includes gum base 408, a center fill 410 (e.g., one of the fill embodiments of the present disclosure) and an exterior coating 412. The pillow or pellet pieces of chewing gum 400 and 406 can be formed using known techniques and methods including those included herein. The exterior coating of pillow or pellet pieces of chewing gum 400 and 406 can be formed using known techniques and methods including taking the uncoated pillow or pellet pieces of chewing gum 400 and 406 and tumbling them repeatedly with, for example, sugar (e.g., powdered sugar) and syrup (e.g., glycerin or corn syrup), allowing the sugar and syrup to dry and repeating the process until a desired thickness of exterior coating is obtained.

Figure 5A:
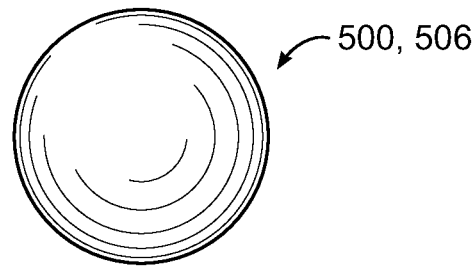
FIG. 5A is illustrative of an exterior perspective view of an exemplary ball or sphere piece of chewing gum embodiment of the present disclosure.
Figure 5B:
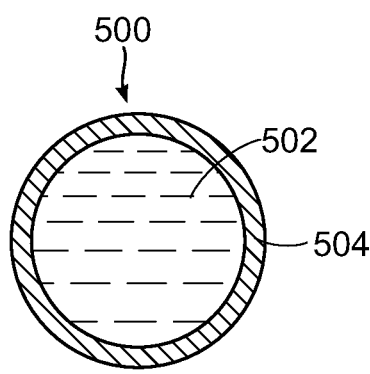
FIG. 5B is illustrative of a cross-section view of one embodiment of an exemplary ball or sphere piece of chewing gum embodiment with an exterior illustrated in FIG. 5A.
Figure 5C:
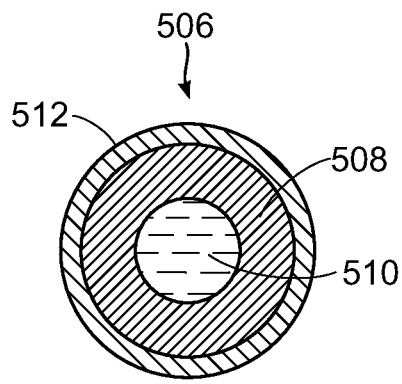
FIG. 5C is illustrative of a cross-section view of another embodiment of an exemplary ball or sphere piece of chewing gum embodiment with an exterior illustrated in FIG. 5A.

Another exemplified embodiment of the present disclosure is illustrated in FIGS. 5A-5C. FIG. 5A is an exterior view of examples of a ball or sphere piece of chewing gum shown in cross-section in FIGS. 5B and 5C. Ball or sphere 500 includes gum base 502 and an exterior coating 504. Ball or sphere 506 includes gum base 508, a center fill 510 (e.g., one of the fill embodiment of the present disclosure) and an exterior coating 512. in the piece of the stick or tab chewing gum 300. The ball or sphere pieces of chewing gum 500 and 506 can be formed using known techniques and methods including those included herein. The exterior coating of ball or sphere pieces of chewing gum 500 and 506 can be formed using known techniques and methods including taking the uncoated ball or sphere pieces of chewing gum 500 and 506 and tumbling them repeatedly with, for example, sugar (e.g., powdered sugar) and syrup (e.g., glycerin or corn syrup), allowing the sugar and syrup to dry and repeating the process until a desired thickness of exterior coating is obtained.

Figure 6:
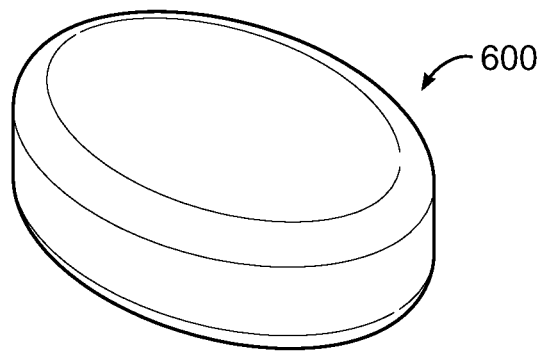
FIG. 6 is illustrative of an exterior perspective view of an exemplary compressed chewing gum embodiment of the present disclosure.

Another exemplified embodiment of the present disclosure is illustrated in FIG. 6. FIG. 6 is an example of a compressed chewing gum 600 that includes gum base in the piece of the compressed chewing gum 600. The piece of the compressed chewing gum 600 can be formed using known techniques and methods including taking gum base material in powdered form and mixing it with chalk (e.g., calcium carbonate) as well as any desired sugar and flavors and putting the resulting mixture in a tablet press to form the piece of the compressed chewing gum 600.

Figure 7:
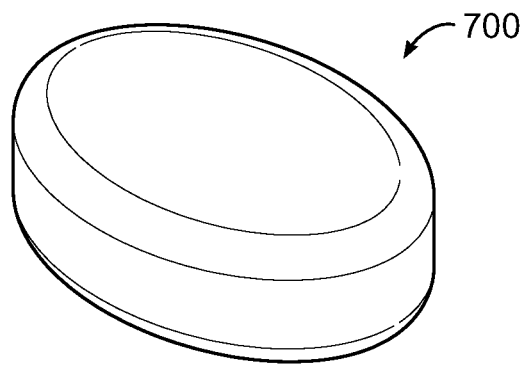
FIG. 7 is illustrative of an exterior perspective view of an exemplary unfilled lozenge embodiment of the present disclosure.

Another exemplified embodiment of the present disclosure is illustrated in FIG. 7. FIG. 7 is an example of an unfilled lozenge 700 including a lozenge candy material.

Figure 8A:
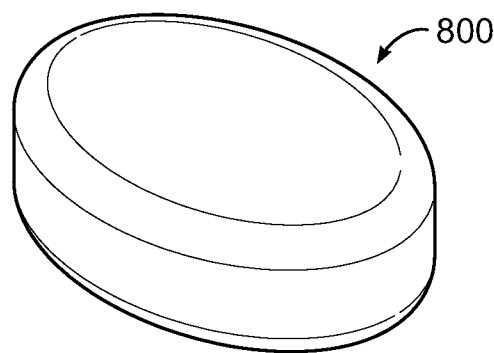
FIG. 8A is illustrative of an exterior perspective view of an exemplary center-filled lozenge embodiment of the present disclosure.
Figure 8B:
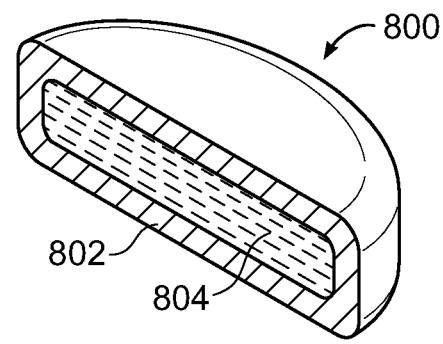
FIG. 8B is illustrative of a cross-section view of the exemplary center-filled lozenge embodiment of FIG. 8A.

Another exemplified embodiment of the present disclosure is illustrated in FIGS. 8A and 8B. FIGS. 8A and 8B is an example of a center-filled lozenge 800 including a shell of lozenge candy material 802 and filling material 804. The filling material 804 can be filling material included in the present disclosure or those know in the art. The filling material can also be a piece of chewing gum base material. Where the filling material is piece of chewing gum base material, the lozenge can be made using known techniques and methods, such as, for example, the gum pieces can be loaded into a heated spherical rotating kettle. Sugar, flavors and food coloring is added which coats the gum layer by layer until the gum piece is to the desired size. To polish, if desired, food grade beeswax or similar is added to the rotating kettle without heat until the desired sheen or smoothness is reached.

Figure 9A:
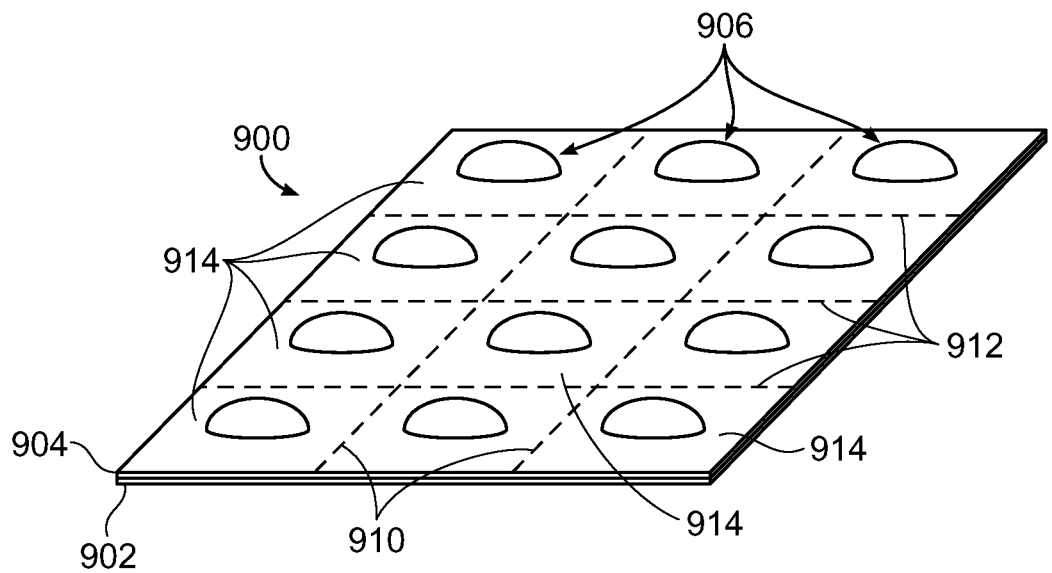
FIGS. 9A and 9B exemplary packaging embodiments of the present disclosure.
Figure 9B:
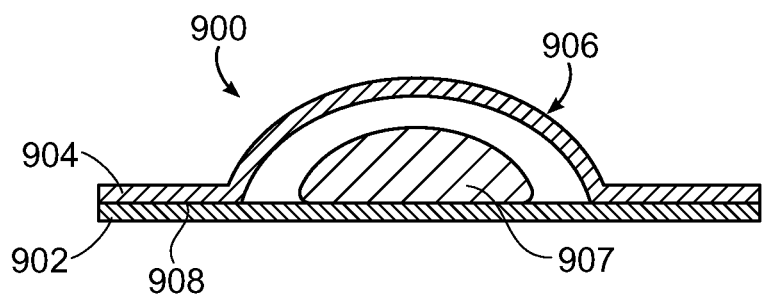

An example of such a kit is a so-called blister pack. Blister packs are well known in the packaging industry and are being widely used for the packaging of pharmaceutical unit dosage forms (chewing gum and lozenge compositions (e.g., chewing gum and lozenges filled and unfilled liquid-filled)). An exemplary embodiment of a blister pack package for containing liquid-filled chewing gum or lozenge embodiments of the present disclosure is shown in FIGS. 9A and 9B. FIG. 9A includes a blister pack sheet and 9B includes a single blister pack in cross-section that makeup blister pack sheet 900 including a sheet of relatively stiff material 902 covered with a foil 904 of a preferably transparent plastic material. During the packaging process recesses 06 are formed in the plastic foil. The recesses 906 have the size and shape of the chewing gum and lozenge compositions (e.g., chewing gum and lozenges that are liquid-filled) to be packed. Next, the chewing gum and lozenge compositions (e.g., chewing gum and lozenges that are liquid-filled) 907 are placed in the recesses 906 and the sheet of relatively stiff material 902 is sealed against the plastic foil at the face of the foil 908 which is opposite from the direction in which the recesses 906 were formed. As a result, the chewing gum and lozenge compositions (e.g., chewing gum and lozenges that are liquid-filled) 907 are sealed in the recesses 906 between the plastic foil 904 and the sheet of relatively stiff material 902. Preferably the strength of the sheet of relatively stiff material 902 is such that the tablets or capsules can be removed from the blister pack by manually applying pressure on the recesses whereby an opening is formed in the sheet of relatively stiff material 902 at the place of the recess. The gum or lozenge can then be removed via said opening. Such blister packs in addition to being a form of packaging the gum or lozenge embodiments of the present disclosure, can also be a way of the consumer keeping track of how many gum or lozenge embodiments of the present disclosure have been consumed in a given period of time (day, week, month, etc) and can include the consumer being able to write or mark on the blister pack package dates or other information to aid in such tracking. The blister pack packaging may also optionally include vertical perforated edges 910 and vertical perforated edges 912 so that the blister pack packaging can be separated into sections 914 containing one of the gum or lozenge embodiments of the present disclosure or multiple sections 914 that are still connected to one another.

The chewing gum and lozenge embodiments of the present disclosure can be filled or unfilled. Filled chewing gum and lozenge embodiments of the present disclosure include a shell material surrounding a fill material, e.g., a center-fill material.

A "lozenge" of the present disclosure can also be in the form of a lozenge or a hard candy but may include lollypops and any other shaped or formed product which can be formed from a core fill component materials and edible shell materials in accordance with the present disclosure.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A chewing gum or lozenge product, comprising:
at least one cannabinoid is in an amount of from about 0.1 wt % to about 10 wt %;
a stabilized menthol composition including a pre-formed mixture of menthol and a menthol stabilizer compound including undecylenic acid methyl ester, wherein the therapeutic composition includes a pain reducing effective amount of menthol.

2. The chewing gum or lozenge product of claim 1, wherein the at least one cannabinoid includes full spectrum hemp oil.

3. The chewing gum or lozenge product of claim 1, wherein the at least one cannabinoid includes less than 0.3 wt % THC.

4. The chewing gum or lozenge product of claim 1, wherein the menthol is in an amount of from about 0.1 wt % to about 14 wt %.

5. The chewing gum or lozenge product of claim 1, further including at least one of an anti-oxidant, a colorant, a flavoring, a flavor enhancer, a preservative, a salivary stimulating agent, a cooling agent, a co-solvent, an emollient, a bulking agent, an anti-foaming agent, a surfactant, a sweetening agent, a filler and a taste-masking agent.

6. The chewing gum or lozenge product of claim 5, wherein the filler is in an amount of from about 15 wt % to about 40 wt % and the sweetening agent is in an amount of from about 0.005 wt % to about 5 wt %.

7. The chewing gum or lozenge product of claim 5, wherein the salivary stimulating agent is citric acid in an amount of from about 0.1 wt % to about 10 wt %.

8. The chewing gum or lozenge product of claim 1, further including an exterior sugar coating.

9. A filled chewing gum or lozenge product including a shell enclosing an internal void therein and a filling in the void, the filled chewing gum or lozenge product comprising:
full spectrum hemp oil in an amount of from about 0.1 wt % to about 10 wt %; and
a stabilized menthol composition comprising a pre-formed mixture of menthol and a menthol stabilizer compound including undecylenic acid methyl ester, wherein the filled chewing gum or lozenge product includes in the stabilized menthol composition menthol in an amount of from about 0.1 wt % to about 14 wt % of the composition.

10. The filled chewing gum or lozenge of claim 9, wherein the filled chewing gum or lozenge product is a unit dose formulation and includes full spectrum hemp oil in a unit dose amount of from about 2 mg. to about 30 mg. and menthol in a unit dose amount of from about 1 mg. to about 20 mg.

11. The filled chewing gum or lozenge of claim 9, the filling further including at least one of an anti-oxidant, a colorant, a flavoring, a flavor enhancer, a preservative, a salivary stimulating agent, a cooling agent, a co-solvent, an emollient, a bulking agent, an anti-foaming agent, a surfactant, a sweetening agent, a filler and a taste-masking agent.

12. The filled chewing gum or lozenge of claim 11, wherein the filler is in an amount of from about 15 wt % to about 40 wt % and the sweetening agent is in an amount of from about 0.005 wt % to about 5 wt %.

13. The filled chewing gum or lozenge of claim 11, wherein the salivary stimulating agent is citric acid in an amount of from about 0.1 wt % to about 10 wt %.

14. The filled chewing gum or lozenge product of claim 9, further including an exterior sugar coating.

15. A method of treating pain of a patient using a chewing gum or lozenge product, the chewing gum or lozenge product being a unit dose formulation and including:
at least one cannabinoid is in an amount of from about 0.1 wt % to about 10 wt %; and
a stabilized menthol composition comprising a pre-formed mixture of menthol and a menthol stabilizer compound including undecylenic acid methyl ester wherein the chewing gum or lozenge product includes menthol in a unit dose amount from about 1 mg. to about 20 mg.,
the method comprising orally administering the chewing gum or lozenge product to an oral cavity of the patient.

16. The method of claim 15, wherein the chewing gum or lozenge product is a filled chewing gum or lozenge product including a shell enclosing an internal void therein and a filling in the void, the shell and the filling including at least one of the at least one cannabinoid and the menthol.

17. The method of claim 15, wherein the chewing gum or lozenge product is a filled chewing gum or lozenge product including a shell enclosing an internal void therein and a filling in the void, the filling including the at least one cannabinoid and menthol.

18. The method of claim 15, wherein the liquid filling further includes at least one of an anti-oxidant, a colorant, a flavoring, a flavor enhancer, a preservative, a salivary stimulating agent, a cooling agent, a co-solvent, an emollient, a bulking agent, an anti-foaming agent, a surfactant, a sweetening agent, a filler and a taste-masking agent.

19. The method of claim 18, wherein the filler is in an amount of from about 15 wt % to about 40 wt % and the sweetening agent is in an amount of from about 0.005 wt % to about 5 wt %.

20. The method of claim 18, wherein the salivary stimulating agent is citric acid in an amount of from about 0.1 wt % to about 10 wt %.

21. The method of claim 15, wherein the at least one cannabinoid includes full spectrum hemp oil.

22. The method of claim 21, wherein the full spectrum hemp oil in a unit dose amount of from about 2 mg. to about 30 mg.

* * * * *